United States Patent
Scott Carnell

(10) Patent No.: US 9,557,322 B2
(45) Date of Patent: Jan. 31, 2017

(54) 3D BIOMIMETIC PLATFORM

(71) Applicant: The United States of America as represented by the Administrator of the National Aeronautics and Space Administration, Washington, DC (US)

(72) Inventor: Lisa A. Scott Carnell, Norfolk, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 265 days.

(21) Appl. No.: 14/316,563

(22) Filed: Jun. 26, 2014

(65) Prior Publication Data
US 2015/0004614 A1     Jan. 1, 2015

Related U.S. Application Data

(60) Provisional application No. 61/839,409, filed on Jun. 26, 2013.

(51) Int. Cl.
*C12N 5/02* (2006.01)
*C12N 5/071* (2010.01)
*G01N 33/50* (2006.01)

(52) U.S. Cl.
CPC ............................. *G01N 33/5073* (2013.01)

(58) Field of Classification Search
None
See application file for complete search history.

(56) References Cited

U.S. PATENT DOCUMENTS

2010/0061962 A1\* 3/2010 Li ........................ A61L 27/18
 424/93.7
2011/0142806 A1\* 6/2011 Scott-Carnell .......... A61L 27/16
 424/93.7

\* cited by examiner

*Primary Examiner* — Michael Burkhart
(74) *Attorney, Agent, or Firm* — Jennifer L. Riley

(57) ABSTRACT

An apparatus and method that utilizes a radiation source and a simulated microgravity to provide combined stressors. The response of cells/bacteria/viruses and/or other living matter to the combined stressors can be evaluated to predict the effects of extended space missions. The apparatus and method can also be utilized to study diseases and to develop new treatments and vaccinations.

20 Claims, 7 Drawing Sheets

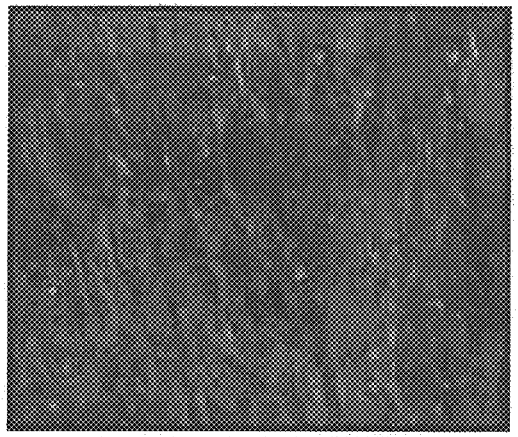
Fig. 6A Fig. 6B
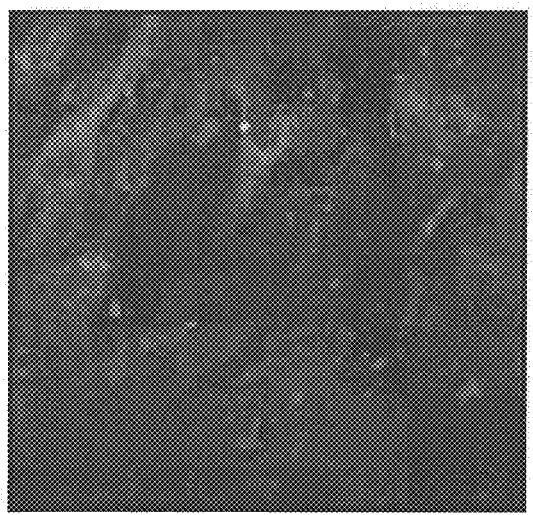
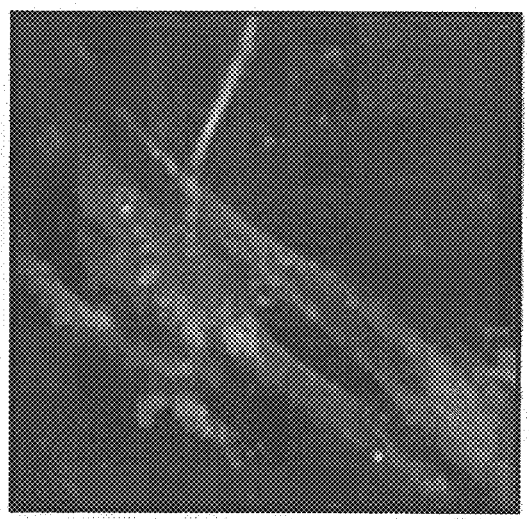
Fig. 7A Fig. 7B

3D BIOMIMETIC PLATFORM

CROSS-REFERENCE TO RELATED PATENT APPLICATION

This patent application claims the benefit of and priority to U.S. Provisional Patent Application No. 61/839,409, titled "3D BIOMIMETIC PLATFORM", filed on Jun. 26, 2013, the contents of which are hereby incorporated by reference in their entirety.

STATEMENT REGARDING FEDERALLY SPONSORED RESEARCH OR DEVELOPMENT

The invention described herein was made by an employee of the United States Government and may be manufactured and used by or for the Government of the United States of America for governmental purposes without the payment of any royalties thereon or therefore.

BACKGROUND OF THE INVENTION

The inability to accurately determine the deleterious effects on the human body after exposure to relevant space conditions is a significant problem in the field of human space flight and exploration. It is often not possible to acquire this data in the actual environment, and conclusions may therefore be drawn and data extrapolated on the health effects anticipated. This method is not reliable because the models used to generate data do not represent in vivo conditions and the effects of individual stressors typically tested neglect the influence of synergistic effects. The effects of the environment in space have also been utilized to develop treatments such as a vaccine for *salmonella*. However, simulating the space environment on the ground has proven to be a significant challenge. One particular challenge has been with reliably correlating ground based data with data obtained on the International Space Station (ISS).

BRIEF SUMMARY OF THE INVENTION

One aspect of the present invention is a ground-based platform that more closely mimics the space environment. A ground-based platform is any platform that is operated in any combination of one or more of the following locations: on and/or in the solid ground of the Earth, on and/or in any body of water on the Earth, and/or within the lower atmosphere of the Earth. In some embodiments the ground-based platform is operated within one or more of the following: on and/or in the solid ground, within the planetary boundary layer, and/or within the troposphere. In embodiments the ground-based platform is operated on and/or in the solid ground and/or within the planetary boundary layer.

The present invention provides a way to simulate the space environment on the ground as closely as possible to evaluate the impact combined exposure to low-dose chronic gamma radiation and simulated microgravity has on the gene expression of human mesenchymal stem cells (hMCSs), and to determine if there is a synergistic relationship between the two stressors. The ground based 3D in vitro platform incorporates synergistic effects from radiation and microgravity and facilitates understanding the mechanistic effects associated with these stressors. A predictive model can be utilized to assess the risks associated with long term space exploration and to allow for the testing of various biological countermeasures. Furthermore, a reliable 3D in vitro platform also allows for individualized screening of astronauts for their radiation adaptability or susceptibility through the use of their own cells.

The combined effects of the two stressors (simulated microgravity and exposure to radiation) can also be utilized to study diseases and develop treatments for diseases and other health-related conditions. Specifically, a 3D Biomimetic test apparatus or platform according to the present invention can be utilized for drug development by correlating ground-based research with research done on a spaced-based platform such as the International Space Station (ISS). For example, when stressed by a spaced-based environment or a simulated space environment according to the present invention (combined radiation and simulated microgravity), bacteria may exhibit an expression of different genes and protective proteins, which is the way that the bacterium protects itself. The protective mechanism of the bacterium becomes more evident, and this information can be utilized to modify the bacterium to create a vaccination or other treatment. A space-based environment or simulated space environment speeds up the vaccination creation process because the bacteria are stressed in a way that it is not stressed on the Earth's surface. The present invention thereby permits more rapid development of vaccines and other treatments utilizing a ground-based platform having significantly reduced cost relative to space-based approaches. Various treatments for diseases, including diseases caused by bacterium and/or viruses, may be developed via the present invention including vaccines, antibiotic drugs, antivirulent drugs and other antibacterial/antivirus medications. In some embodiments the disease is caused by at least one bacterium. In one embodiment the treatment is a vaccine.

Exposure to chronic low-dose gamma radiation in simulated microgravity is believed to result in synergistic effects. The combined stressors are believed to work in synergy with each other to intensify the effect of each individual stressor. Accordingly, one aspect of the present invention involves exposing a 3D scaffold comprising one or more of layers of electroactive fibers to radiation while the 3D scaffold is simultaneously subjected to simulated microgravity. The present invention may utilize gamma radiation at very low dose rates to provide chronic exposure to radiation. Microgravity may be simulated utilizing a known rotating wall vessel bioreactor to provide for ground based microgravity experiments. The simulated microgravity bioreactor may be positioned in a radiation field to obtain data on the combined effects of radiation and microgravity. Focused microarrays may be utilized to determine the influence on differentiation and to examine changes such as oxidative stress effects, DNA damage signaling, apoptosis and heat shock protein response. These studies can be used to isolate the mechanisms associated with each individual stressor and the influence of combining the stressors in a more appropriate space simulated environment.

In vitro studies preferably include the relevant biological environment pertaining to the cells/tissues being studied in vivo. A novel biomimetic 3D scaffold capable of delivering biochemical, mechanical, electrical, architectural and topographical cues during culture which more closely mimic the native environment is described in United States Patent Application Publication No. 2011/0142806. This biomimetic 3D scaffold may be compared to conventional 3D microcarrier beads currently used for the evaluation of cells in simulated microgravity. This comparison may be utilized to provide an understanding of the role morphology plays when exposed to external stressors.

One aspect of the present invention involves determining the effect on gene expression for human mesenchymal stem cells cultured in simulated microgravity using a biomimetic 3D scaffold.

A second aspect of the present invention involves determining the effect on gene expressing for human mesenchymal stem cells cultured in a chronic low-dose gamma radiation environment using a biomimetic 3D scaffold.

A third aspect of the present invention involves determining the effect on gene expression for human mesenchymal stem cells cultured in a combined simulated microgravity and chronic low-dose gamma radiation environment using a biomimetic 3D scaffold.

A fourth aspect of the present invention involves determining the effect on human mesenchymal stem cells cultures as in the third aspect with a "return to earth" stressor by allowing the cell cultures to re-adapt prior to analyzing the gene expression.

Embodiments of the invention include an assembly for identifying the combined effects of microgravity and radiation, wherein the assembly includes a bioreactor capable of simulating reduced gravity in a test space of the bioreactor, and a radiation source configured to provide radiation whereby cells and/or bacteria and/or viruses disposed in the test space are exposed to radiation. In some embodiments, the assembly is a ground-based assembly/platform.

Some embodiments of the invention are a test assembly for testing the combined effects of microgravity and radiation. The test assembly includes at least a bioreactor capable of simulating reduced gravity in a test space of the bioreactor; a radiation source configured to provide radiation whereby cells and/or bacteria and/or viruses disposed in the test space are exposed to radiation.

Another embodiment of the invention is a ground-based method of determining a response to combined environmental stressors, wherein the method provides a cell culture; and exposes the cell culture to radiation from a radiation source while the cell culture is simultaneously exposed to simulated microgravity.

Still other embodiments of the invention are a method of determining a response to combined environmental stressors, wherein the method includes providing a cell culture; exposing the cell culture to radiation from a radiation source while the cell culture is simultaneously exposed to simulated microgravity. In one embodiment this method is a ground-based method that is performed on a ground-based assembly/platform.

These and other features, advantages, and objects of the present invention will be further understood and appreciated by those skilled in the art by reference to the following specification, claims, and appended drawings.

BRIEF DESCRIPTION OF THE SEVERAL VIEWS OF THE DRAWINGS

FIG. 6A is an image of cytoskeleton protein expression F-actin (green) and intermediate filament protein vimentin (red) with the nuclei (blue) for hMSCs after seven days in culture on a 2D surface;

FIG. 6B shows an image of cytoskeleton protein expression F-actin (green) and intermediate filament protein vimentin (red) with the nuclei (blue) for hMSCs after seven days in culture on a 3D fiber scaffold;

FIG. 7A is an image showing expression of gap-junction protein connexin-43 (green) and focal adhesion protein vinculin (red) for hMSCs after fourteen days in culture on a 2D surface;

FIG. 7B is an image showing expression of gap-junction protein connexin-43 (green) and focal adhesion protein vinculin (red) for hMSCs after fourteen days in culture on a 3D fiber scaffold;

DETAILED DESCRIPTION OF THE INVENTION

Figure 1:
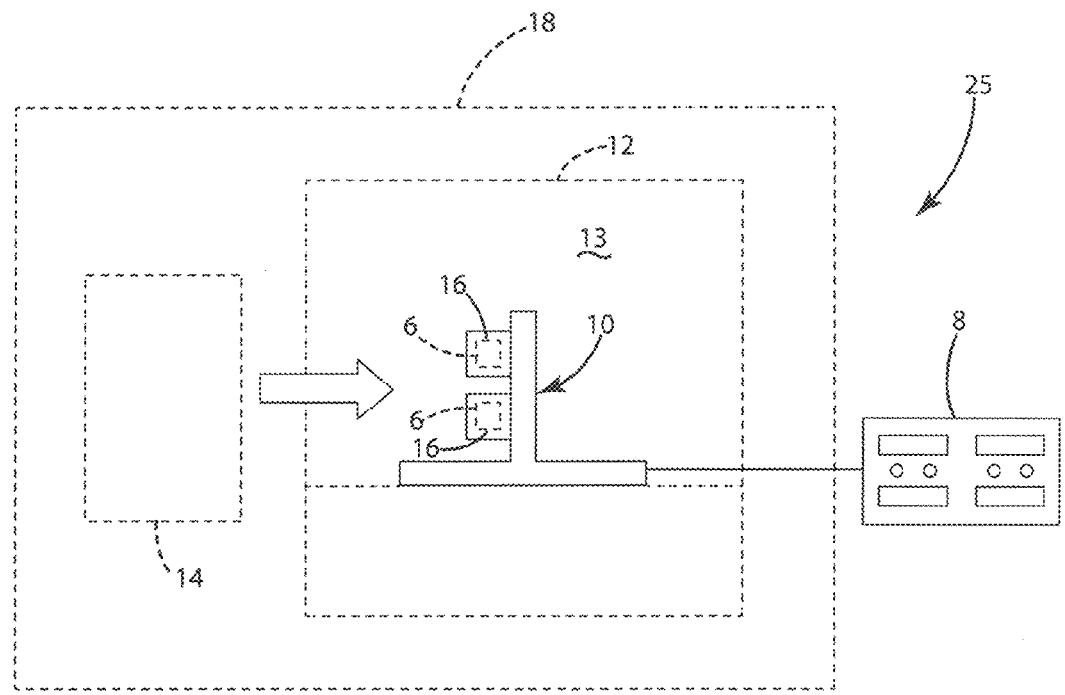
FIG. 1 is a schematic view of a rotating bioreactor and radiation source/environment according to one aspect of the present invention.

For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Future human space missions will require crew to travel beyond low earth orbit (LEO) for extended periods of time exposing them to the harsh space environment which poses both acute and chronic risks to crew health and safety that have clinically relevant implications for their lifetime. Two of the primary environmental stressors creating health challenges for crew are radiation and microgravity. Galactic cosmic rays (GCR) are ubiquitous in space and generate a mixed field of ionizing radiation that is difficult to shield against. In low earth orbit, there is significant protection from the Earth's magnetosphere; even so, the International Space Station ("ISS") averages a chronic low-dose rate of 500 μGy/day with modest shielding measures in place. Microgravity has been known to cause health issues for astronauts long after their return to earth. Several studies have been performed using a known simulated microgravity bioreactor in order to understand the space environment better and develop appropriate countermeasures. Correlating the ground based results using the simulated microgravity bioreactor to those obtained in space has proven to be a challenge. Part of this challenge is due to the low level radiation stressor that is chronically present during the space studies yet absent when performed on the ground.

In vitro models are ideal for developing fundamental knowledge of biological mechanisms and are relatively inexpensive compared to in vivo studies. However, in order to derive true meaning from the data, it may be necessary to replicate the in vivo environment as closely as possible. As discussed in more detail below, the present invention utilizes a 3D biomimetic scaffold system that mimics in vivo conditions.

One aspect of the present invention is a representative space analog that permits in vitro experiments to determine differences due to each individual stressor, microgravity and radiation, and to examine the combination of the stressors to establish if the effect is synergistic and the underlying mechanisms associated with each stressor.

Some studies concerning the effects of simulated microgravity on hMSCs have been conducted. Simulated microgravity reportedly reduces the expression of collagen type I, ALP and ERK activation, increases markers for adipocyte differentiation and induces p38 activation in hMSCs. In one study hMSCs were cultured for a period of seven days to evaluate the osteoclastogenesis and osteoblastogenesis using a known simulated microgravity bioreactor. The results showed that the environment inhibited osteoblastogenesis even with osteogenic induction and increased adipocyte differentiation. The hMSCs differentiation profile and gene expression following exposure to simulated microgravity (in the absence of applied low dose radiation) may be examined to determine the effect on various genes and pathways.

Some studies concerning low-dose radiation effects on hMSCs have also been conducted. Cellular studies with ionizing radiation have shown cytotoxic effects for high doses (>2 Gy) and transcriptional effects at low doses (<2 Gy). Jin et al exposed hMSCs to very low doses: 0.01, 0.05, 0.2 and 1 Gy of gamma radiation and performed microarray analysis at four different timepoints: 1, 4, 12, and 48 hours post-irradiation. Results showed a non-linear pattern in cellular activity with respect to dose. According to one aspect of the present invention, experiments may be performed at 3 different doses and 3 different time points. Several genes associated with cellular stress response may be analyzed to help determine if a non-linear pattern exists. Genetic changes may be examined immediately post-irradiation to assess the effects of chronic radiation.

It is generally believed that microgravity enhances the effect of radiation though synergistic effects that have not been effectively established. Manti et al exposed peripheral blood lymphocytes to X-rays at doses between 0-6 Gy then cultured them in a rotating wall vessel microgravity bioreactor to determine the synergistic effects. Another group exposed human fibroblasts to γ irradiation prior to the space mission to determine synergistic effects. True synergy; however, requires exposure to radiation and microgravity simultaneously due to the sensitive nature of biological processes. The present invention achieves synergy on the ground by subjecting a rotating wall vessel (RCCS) bioreactor to chronic low-dose gamma radiation simultaneously throughout the experiment. Gene expression may be analyzed immediately following exposure to the combined stressors as well as at multiple time points post-irradiation to provide the cells with a pseudo return to earth (gravity) environment to include the adaptation effects that may be experienced by the Crew. I expect to see an influence in both gene and protein expression compared to the individual stressors of microgravity and gamma radiation in addition to the return to earth environment.

Cell culture has conventionally been performed in a dish which offers a 2D environment that does not take in vivo conditions into consideration since the body exists in three dimensions. In the 1980's the concept of culturing cells on synthetic scaffolds paved the way for a new research area in scaffolds for tissue engineering and began a quest for the ideal biomaterial and the development of biomimicking 3D scaffolds. A great deal of attention was focused on the development of biodegradable scaffolds that could be tailored such that their degradation properties would depend on the cell culture time and the organ in which they were targeting. Common materials include polyglycolic acid (PGA), polyethylene glycol (PEG), polylactic-glycolic acid (PLGA), polyurethane, polycaprolactone (PCL), chitosan, collagen, hyaluronic acid, hydroxyapatite and elastin-like polymer.

The goal in scaffold fabrication is to create an environment that mimics the native tissue in vivo for optimal in vitro regeneration. Current trends have focused on the development of biofunctional materials and scaffolds, i.e. the ability to apply stimuli to the cells in vitro. The stimuli can be one of several forms such as a change in pH or temperature, delivery of growth factors, proteins or DNA upon scaffold degradation, and immobilization of functional groups on the surface to promote cell attachment or cell-substrate interactions. Fabrication of scaffolds has advanced rapidly over the past two decades resulting in a variety of techniques to produce novel scaffolds for cell culture. There are three popular forms of scaffold constructs that provide a 3D environment, gels, microcarrier beads and macroporous fibrous structures. Gels produced from collagen, fibrin, gelatin, and alginate demonstrate favorable results compared to conventional 2D systems when used to culture specific cell types; however, they are not ideal for use in the microgravity bioreactor. Microcarrier beads have been used successfully in several studies to create an environment for cell attachment in the microgravity bioreactor. Scaffolds fabricated from fibers with diameters ranging from nanometers to micrometers have also been investigated extensively as 3D constructs, however; few studies have employed this particular design as their model in the microgravity bioreactor. There are several techniques available that produce 3D structures though obtaining the ideal combination of feature size, controlled porosity and material selection is still under investigation.

One promising processing technique that has the ability to tailor all three areas is electrospinning. Electrospun scaffolds have been fabricated from a multitude of biocompatible polymers with size features ranging from micro to nanometer. The fibers formed, particularly those with nanoscale diameters, may represent much of the connective tissue found in vivo. Aligned fibers have been investigated extensively and shown to promote cell alignment and attachment due to their high surface to volume ratio. Studies suggest that a fibrous structure plays a fundamental role in the modeling of the extracellular matrix and overall gene expression. The porosity can be controlled enough to allow for ample exchange of nutrients, waste and oxygen to the cells, thus electrospinning has been chosen as the method to produce scaffolds for analysis in this particular study.

Recent studies have reported significant differences in the end points observed when comparing 2D and 3D in vitro models exposed to ionizing radiation. In a study performed by Zschenker et. al., two human cancer cell lines, A549 lung cancer cells and UT-SCC15 head and neck squamous cell carcinoma, were seeded on 3D spheroids and compared to the conventional 2D culture dish after exposure to various X-ray doses ranging from 0-6 Gy at 200 kV. The researchers found little difference in DNA repair when comparing the 2D and 3D environments but noted significant changes in biological functions such as tissue development, cell adhesion and defense response between them. Their results emphasize the importance of studying cell culture in a 3D environment and the profound impact the in vitro environment has on gene expression. The researchers also noted the importance of the environment on cell-cell communication since it is strongly influenced by cell-extracellular matrix contacts which were significantly affected when comparing the 2D and 3D in vitro environments. It is important to understand not only the architectural but the topographical, mechanical, electrical and biochemical influences on the cell-extracellular matrix relationship. As evidenced in the work reported by Cordes and Beinke, the cell culture matrix played a central role in the radiation response for p53 wild-type A5A9 lung cancer cells when cultured on fibronectin, polystyrene and bovine serum albumin. They reported a higher survival rate for cells cultured on fibronectin compared to the other cell culture models. This is an important finding that needs to be factored in during in vitro observations since multiple models are typically employed to study radiation effects. A 3D fiber scaffold system according to the present invention can be compared to 3D microcarrier beads which will allow a preliminary comparison regarding this aspect. The difference between 2D and 3D cell culture environments and their influence on the extracellular matrix as well as cell-cell communication may also be examined.

The present application is related to United States Patent Application Publication No. 2009/0108503 filed on Jun. 2, 2008, United States Patent Application Publication No. 2010/0201384 filed on Feb. 10, 2010, United States Patent Application Publication No. 2010/0211151 filed on Feb. 3, 2010, and United States Patent Application Publication No. 2011/0142806 filed on Dec. 15, 2010, the entire contents of each of which is incorporated herein by reference. These patent publications describe a modified electrospinning process that controls fiber deposition to produce aligned fibers and mats. Using this technique, aligned electroactive fibers and mats have been fabricated from polyvinylidene fluoride (PVDF) polymer. The pyroelectric properties of the fibers have contributed to the differentiation of human mesenchymal stem cells in preliminary laboratory studies.

With reference to FIG. 1, a test set-up 25 according to one aspect of the present invention includes a bioreactor 10 that simulates zero gravity and/or microgravity. In the illustrated example, a known rotating wall bioreactor 10 having one or more rotating test spaces 16 is utilized. As used herein, the term "bioreactor" generally means any device or combination of devices that are capable of simulating zero gravity and/or microgravity. Cell cultures 6 are disposed in the rotating test spaces 16. Cell cultures 6 may comprise virtually any living matter and/or viruses. For example, cell cultures 6 may comprise human, plant, or animal cells (e.g. stem cells), bacteria, and/or viruses. In use, the rotating test spaces 16 rotate to thereby expose the cell cultures 6 to a simulated microgravity environment. The bioreactor 10 may comprise a known rotating wall vessel bioreactor including a control unit 8 that provides for control and monitoring of the bioreactor 10 during testing. As discussed in more detail below, the cell cultures 6 may comprise three dimensional fibrous scaffolds that mimic an in vivo environment, whereby cells are cultured on the scaffold. Alternatively, cell cultures 6 may comprise 2D cell cultures.

Referring again to FIG. 1, the bioreactor 10 may be positioned inside an incubator 12 having an interior space 13 providing a controlled temperature as may be required for a particular application. The incubator 12 may be positioned inside a test facility 18 that includes a radiation source 14 that is in line with incubator 12 such that the cell cultures 6 in rotating test spaces 16 are exposed to gamma radiation "R" from radiation source 14. Radiation source 14 may comprise a known low-dose gamma radiation source providing about 500 µGy/day. Thus, the test set-up 25 permits the cell cultures 6 to be simultaneously exposed to simulated microgravity and low dose gamma radiation for a predefined period of time. The cell cultures 6 may be simultaneously exposed to low dose gamma radiation and simulated microgravity utilizing test set-up 25 for periods of time ranging from, for example, 24 or 48 hours to 7 or 14 days. The cell cultures 6 may be simultaneously exposed to low dose gamma radiation and simulated microgravity for longer periods of time (e.g. months or years) if required for a particular test or research project. According to other aspects of the present invention, cell cultures 6 may be exposed to radiation and microgravity in a sequential or alternating manner. For example bioreactor 10 may be activated for a first period of time while the radiation source 14 is deactivated or moved away from bioreactor 10 such that cell culture 6 is only subjected to microgravity during the first time period. After the first period of time has passed, the radiation source may then be activated or moved into the vicinity of bioreactor 10 for a second period of time while the bioreactor is deactivated (or while the cell cultures may be removed from bioreactor 10). The first and second time periods may be equal, or they may be significantly different.

Radiation source 14 may also be configured to provide higher dose gamma radiation and/or other radiation. For example, radiation source 14 may be configured to provide ionizing radiation that is substantially similar to radiation that exists outside the earth's atmosphere.

Figure 2:
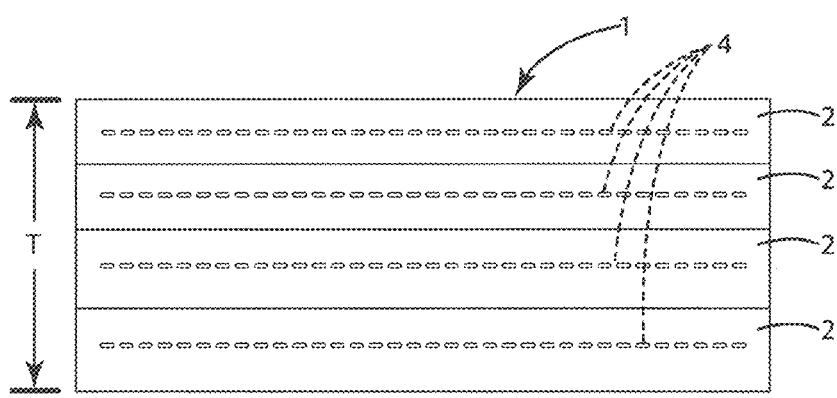
FIG. 2 is a schematic view of a three dimensional (3D) scaffold according to one aspect of the present invention.

With further reference to FIG. 2, a three dimensional scaffold 1 according to one aspect of the present invention may comprise a plurality of layers 2, wherein each layer 2 comprises a plurality of fibers 4. The fibers 4 may be oriented to provide an alternating 0°/90° layup. Although four layers 2 are shown in FIG. 2, it will be understood that the 3D scaffold 1 may comprise significantly more layers (e.g. 30-100 or more layers). The fibers 4 may comprise electrospun polymer fibers as disclosed in U.S. Patent Publication No. 2009/0108503. For example, the fibers 4 may comprise electrospun polyvinylidenefluoride (PVDF) polymer. The 3D scaffold 1 may comprise an electroactive scaffold as disclosed in U.S. Patent Publication No. 2011/0142806. However, it will be understood that the present invention is not limited to a particular material composition with respect to the fibers 4, and various polymer materials or other materials may be utilized in 3D scaffold 1 as may be appropriate for a particular application. Still further, it will be understood that the 3D scaffold 1 could comprise a variety of fibrous or non-fibrous macroporous structures. In general, the 3D scaffold 1 has a sufficient thickness "T" to mimic a native environment.

In a preferred embodiment, the cell cultures 6 include a 3D scaffold 1 and cells such as human mesenchymal stem cells or other cells and/or viruses. During testing, the 3D scaffold 1 is disposed in the rotating test spaces 16 such that the 3D scaffold 1 rotates with the test spaces 16. As discussed in more detail below, the effects of the combined microgravity and radiation exposure can be evaluated to determine the response of the cells in the cell cultures 6.

Figure 3:
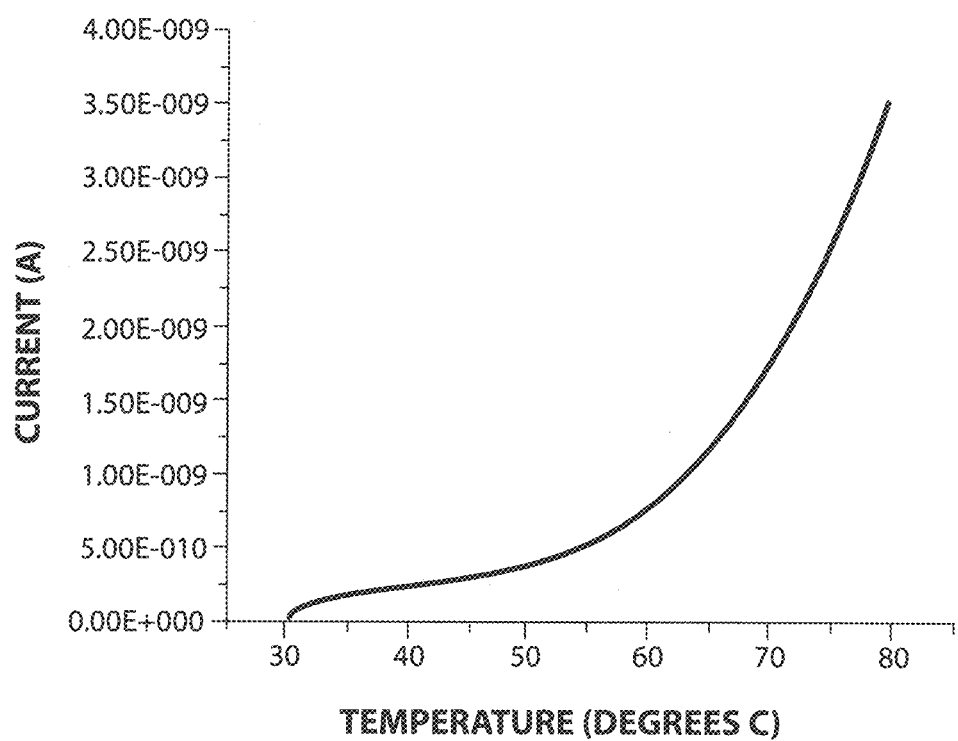
FIG. 3 is a graph showing the pyroelectric profile of beta phase PVDF.

A 3D fiber scaffold according to one aspect of the present invention mimics the in vivo environment more closely by delivering the requisite biochemical, mechanical, electrical and topographical cues during culture and will provide more realistic data using an in vitro model to determine the intracellular signaling, cell-cell communication, and cytoskeleton formation and motility. The 3D fiber scaffold is fabricated from a ferroelectric polymer, poly vinylidene fluoride (PVDF) that generates a slight current during culture at 37° C. due to its intrinsic pyroelectricity. The pyroelectric profile for the beta phase (polar) of this material is illustrated in FIG. 3. Electrical stimulation has been implicated in three key areas on the cellular level including the physical environment, growth factors and signal transduction cascade. However, incorporating electrical stimuli during cell culture has been virtually overlooked until recently. A 3D scaffold according to aspects of the present invention may include aligned fibers which represent much of the connective tissue found in vivo and it is porous enough to allow for ample exchange of oxygen, nutrients and waste during culture.

A 3D in vitro model according to another aspect of the present invention may comprise multiple layers, of aligned electroactive fibers. An external electric field can be applied to the fibers of each layer in vitro. In vitro studies utilizing an applied voltage of 10 mV have shown a significant influence on the differentiation of human mesenchymal stem cells. This is relevant because much of the in vivo tissue and cells are electrically active. The ability to vary the voltage and apply it to the individual layers allows the researcher to tailor the electrical influence based on the tissue/cell of interest. This model can be used to perform synergistic experiments on human cell lines and aids in the development and assessment of biological countermeasures, risk prediction models and individualized astronaut screening.

Human mesenchymal stem cells (hMSCs) are an ideal cell line for use in a study according to the present invention due to their multipotent capability to differentiate into various lineages in vitro and for their therapeutic potential. Furthermore, hMSCs have been explored extensively for the assessment of osteogenesis in vitro. Since they have been studied in vitro in both simulated microgravity and in space there is previously reported data with which to compare the results of the present invention. hMSCs may be isolated from bone marrow, seeded on tissue culture polystyrene plates and cultured with antibiotics using Dulbeccos Modified Eagle's Medium and fetal calf serum for 7 days at 37° C. in 5% CO2 environment. To date there is little data on the influence of the in vitro environment during exposure to ionizing radiation. The in vitro environment is a critical component that will influence intracellular signaling, cell-cell communication, and cytoskeleton formation and must be examined critically for data generated to be relevant.

Several research groups have employed whole genome analysis to examine effects of disease or stressors in their studies. This is an excellent technique that comes with a host of challenges. There are more than 33,000 genes to be analyzed creating a much larger pool of data and requiring significantly more time to analyze and interpret the data. Focused microarrays arose as a simplified high-throughput platform that allows the researcher to focus in on particular pathways or diseases without needing extensive microarray systems and software to generate and analyze the data. The focused microarrays can be performed using a real-time PCR machine and the data can be analyzed and interpreted in hours or days as opposed to months. Wurmbach et al. performed a study to analyze focused microarrays and reported greater sensitivity and accuracy with excellent repeatability. Focused microarrays (available from SA Bioscience) may be utilized in studies according to the present invention. These microarrays include 84 genes and multiple housekeeping genes spanning various pathways depending on the area of interest. Utilization of focused microarrays from a commercial supplier allows the research to be repeated much more readily in an independent laboratory for verification.

A first object of the present invention is to determine the effect on gene expression for human mesenchymal stem cells cultured in simulated microgravity using a biomimetic 3D scaffold. Studies/processes according to the present invention may utilize 3D microcarrier beads as the standard control and a 3D fiber scaffold to culture hMSCs in a microgravity bioreactor to determine the effect of simulated microgravity. Gene expression changes may be evaluating using qPCR focused microarrays after multiple time points: 72 hours, 7 days and 14 days. RNA may be extracted immediately using a commercially available RNEASY minikit (Qiagen) following each time point to detect changes associated with the microgravity stressor. The qPCR focused microarrays may be utilized to examine pathways associated with cell stress and disease, DNA damage, and the cell cycle. Since hMSCs are known to differentiate into various lineages, stem cell differentiation focused microarrays may also be run to assess the impact of this environment on their differentiation. The gene expression changes for hMSCs cultured on 3D microcarrier beads and fiber scaffold under static conditions at the same time points may be utilized as a reference. hMSCs cultured in tissue culture polystyrene may be included in the experiments/processes to provide an additional baseline control. The resulting data may be statistically analyzed using analysis of variance (ANOVA).

To observe the effects of radiation on the cytoskeleton, samples may be fixed in 4% PFA, permeabilized with 0.25% Triton-X 100 and stained for immunofluorescence imaging of cytoskeleton proteins F-actin and intermediate filament protein vimentin with the nuclei counterstained using DAPI. Cell-cell communication may be examined by immunostaining for connexin-43. Confocal laser scanning microscopy may be used to observe cell morphology, cytoskeleton and cell-cell communication proteins. Protein expression may be determined for each sample of interest using Western Blot. Cells may be lysed using RIPA buffer containing protease inhibitor at the pertinent timepoints determined post-irradiation. Total protein concentration may be quantified using a bicinchoninic acid (BCA) kit. Protein samples (10 µg) containing 2× Laemmli buffer may be loaded in polyacrylimide ready gels and electrophoresis run using SDS-PAGE buffer. The protein may be transferred from the gel to a nitrocellulose membrane using an electrophoresis chamber in a cold room. The nitrocellulose membrane may be placed in a blocking mixture of 5% nonfat milk in TBS containing 0.1% Tween for a minimum of 1 hour prior to the addition of the primary antibodies. Primary antibodies may be incubated overnight in the cold room. The samples may be washed 3× then incubated with the secondary antibodies for a minimum of one hour. After the samples have been washed 3×, the antibody detection solution may be added to the membrane and incubated for 5 minutes. The membrane may be exposed to the camera without a filter for two time periods, 5 minutes and 10 minutes using a Kodak® Gel Logic 200. The protein of interest may be analyzed using the Kodak® Imaging software by normalizing the protein band to the housekeeping protein GAPDH.

A second objective of the present invention is to determine the effect on gene expression for human mesenchymal stem cells cultured in a chronic low-dose gamma radiation environment using a biomimetic 3D scaffold. Studies/processes according to the present invention may use 3D microcarrier beads as the standard control and a 3D fiber scaffold to culture hMSCs in tissue culture plates, and determine the effect of low-dose Co-60 gamma radiation at 3 different total doses: 0.25 Gy, 0.5 Gy, and 1 Gy. These dose levels are consistent with permissible exposure limits established for the astronaut core and those expected on missions. Gene expression changes may be evaluated using qPCR focused microarrays after multiple time points: 72 hours, 7 days and 14 days of chronic radiation exposure. RNA may be extracted immediately following each time point to detect changes associated with chronic radiation exposure. As a reference, the gene expression changes for hMSCs cultured on 3D microcarrier beads and 3D fiber scaffold in the absence of radiation at the same time points may be determined. hMSCs cultured in tissue culture polystyrene may be included in the experiments to provide an additional baseline control. Data may be statistically analyzed using analysis of variance (ANOVA). The data generated will also facilitate the development of a low-dose profile dose response curve.

Proteins of interest may be examined by immunostaining, visualized with confocal microscopy imaging and confirmed by western blot. The protocol may be similar to that described above in connection with the first objective.

The chemical and topographical features of the scaffold play a critical role in the formation of the extracellular matrix and contribute to cell-cell communication. Alterations in the in vitro scaffold environment due to radiation may play a role in differences observed in the cytoskeleton as well as the long term effects resulting from cell signaling adaptation. The influence of the different 3D cell culture models may be examined by exposing the cell culture scaffold alone to radiation and examining the surface effects to determine if there is a significant alteration in the cell culture environment that may be contributing to the results. To assess the contribution of the in vitro environment, cell culture models including polystyrene (2D), 3D microcarrier beads and 3D fiber scaffolds may be exposed to the same dose and LET radiation used in connection with the first objective. Surface properties of each model will be analyzed using Fourier Transform Infrared Spectroscopy (FTIR) and imaged using scanning electron microscopy (SEM) to determine changes in the surface features and chemical composition post-irradiation.

A third objective of the present invention is to determine the effect on gene expression for human mesenchymal stem cells cultured in a combined simulated microgravity and chronic low-dose gamma radiation environment using a biomimetic 3D scaffold. 3D microcarrier beads may be used as the standard and a 3D fiber scaffold to culture hMSCs, and determine the effect of simulated microgravity combined with chronic low-dose Co-60 gamma radiation at 3 different total doses similar to those of the second objective: 0.25 Gy, 0.5 Cry and 1 Gy. The experimental set-up described in connection with the third objective has been evaluated using dosimeters in a low-dose Co-60 gamma radiation facility. The microgravity bioreactor may be housed in an incubator fitted with a glass door positioned at a designated point away from the source to achieve the total dose/dose rate desired. The incubator may remain in the radiation field throughout the entire experiment providing a chronic low-dose radiation exposure. Gene expression changes may be evaluated using qPCR focused microarrays after multiple time points of chronic radiation exposure similar to the first objective: 72 hours, 7 days and 14 days. RNA may be extracted immediately following each time point to detect changes associated with the combined stressors. As a reference, the gene expression changes for hMSCs cultured on 3D microcarrier beads and 3D fiber scaffold under static conditions with and without radiation at the same time points. hMSCs cultured in tissue culture polystyrene may be included in all experiments to provide an additional baseline control. All data may be statistically analyzed using analysis of variance (ANOVA).

Proteins of interest may be examined by immunostaining, visualized with confocal microscopy imaging and confirmed by western blot. The protocol to be performed may be similar to that described in connection with the first objective.

A fourth objective is to determine the effect on human mesenchymal stem cells cultured as in the third objective with a 'return to earth' stressor by allowing the cell cultures to re-adapt prior to analyzing the gene expression. In order to protect humans from the deleterious effects of space it is necessary to consider post-flight changes that they may experience upon return to earth. Several studies have investigated the effect of radiation or microgravity after the cells have had a period of time to repair or adapt. The previous aims represent more closely the environment experienced by humans during a space mission but do not account for the return to earth and cellular changes associated with that stressor. For these studies, experiments will be performed as in the third objective; however, following exposure to chronic radiation, cell cultures are returned to a gravity environment without radiation exposure and gene expression is analyzed after 24 and 48 hours post-irradiation. This provides information on the adaptation of the cell cultures to the space simulated environment.

Figure 4A:
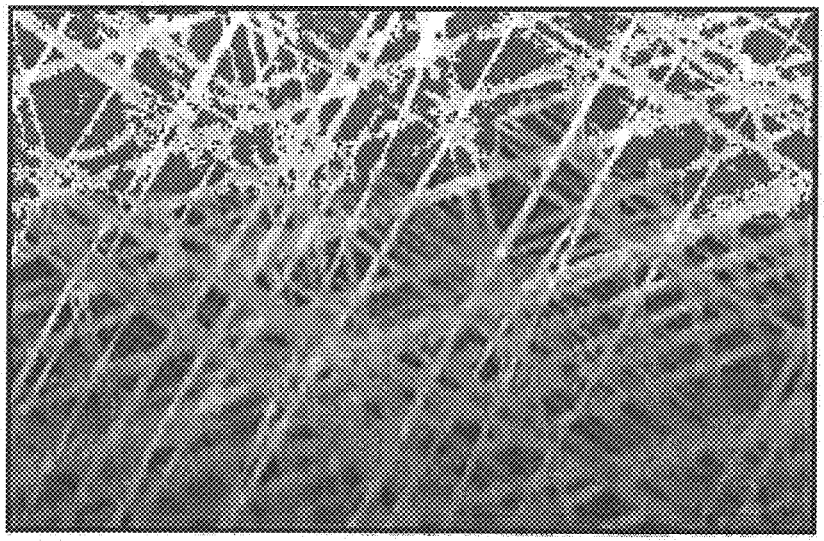
FIG. 4A is an optical microscopy image of an electrospun 3D fiber scaffold.
Figure 4B:
FIG. 4B is an optical microscopy image illustrating live/dead assay results for human mesenchymal (hMSC) for hMSCs cultured for seven days on the scaffold of FIG. 3A.
Figure 5:
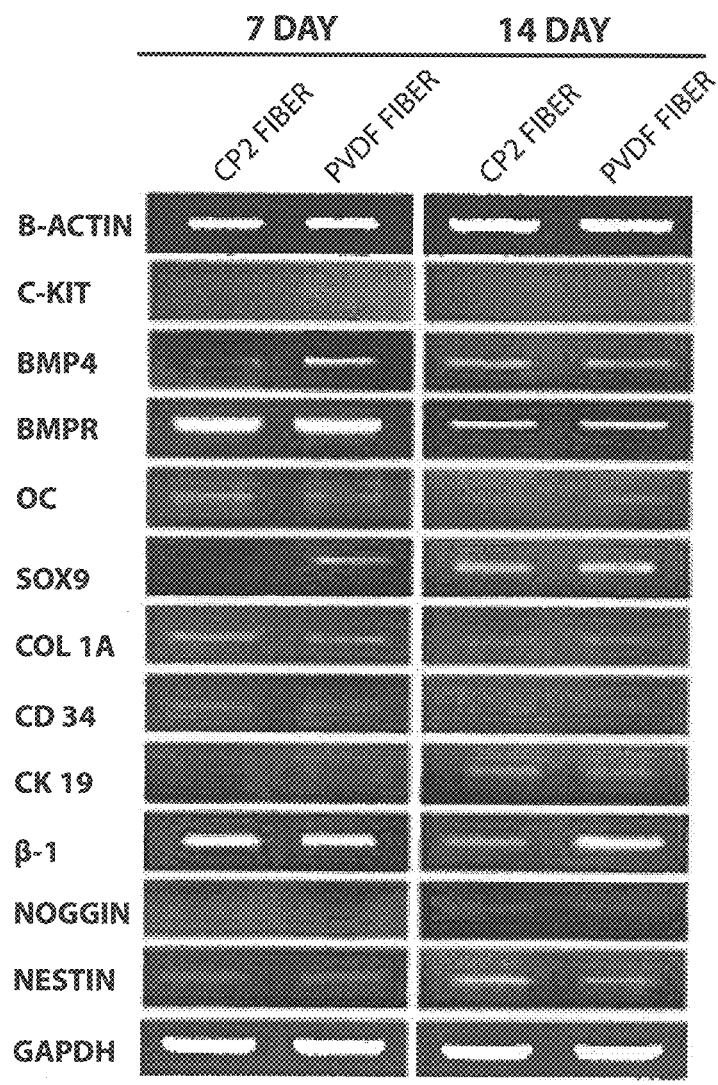
FIG. 5 shows gene expression after seven and fourteen days in vitro for a 3D fiber scaffold.
Figure 8:
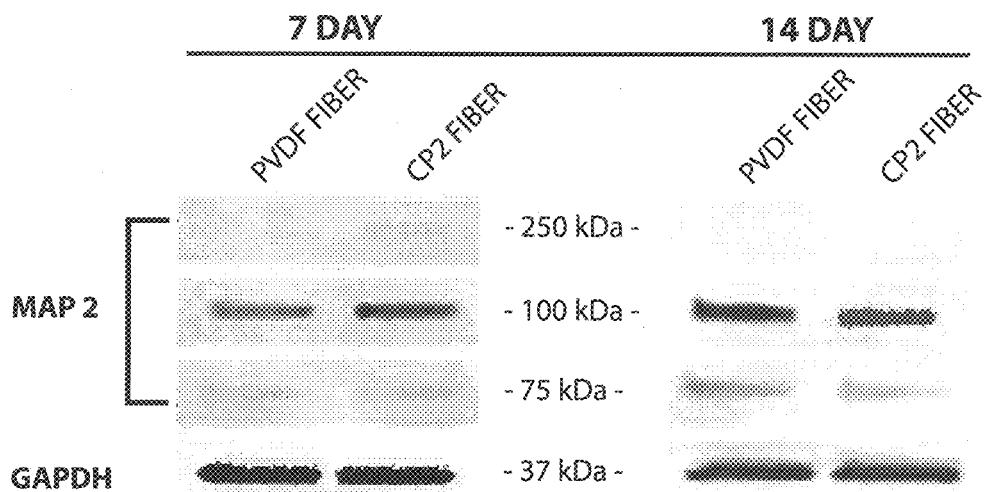
FIG. 8 is a western blot gel image illustrating protein expression after seven and fourteen days for hMSCs cultured on CP2 and PVDF fibers.

3D fiber scaffolds mimic the in vivo environment more closely than conventional cell culture models by delivering the requisite biochemical, mechanical, electrical and topographical cues during culture and provide more realistic data using an in vitro model to determine the intracellular signaling, cell-cell communication, and cytoskeleton formation and motility. 3D fiber scaffolds with semi-controlled porosity consisting of highly aligned fibers (FIG. 4A) have been developed for in vitro tissue engineering applications. Live/dead assay (FIG. 4B) confirmed human mesenchymal stem cells (hMSCs) attach and proliferate on the aligned fibers. Preliminary studies comparing the influence of a 2D environment to a 3D fiber scaffold show a significant influence on gene and protein expression for human mesenchymal stem cells (hMSCs) after 7 and 14 days in culture. Examination of 28 genes representing the mesoderm, endoderm and ectoderm layers resulted in upregulation of 17 genes on the 2D surfaces (not shown), indicative of a heterogenous population, while the 3D scaffold upregulated 10 genes, just over half as many (FIG. 5). This indicates significant 3D fiber scaffold differences in cell-cell signaling and extracellular matrix formation and suggests the fiber scaffold is playing a role in cytoskeleton organization and intermolecular signaling. Immunofluorescence imaging of F-actin and intermediate filament protein vimentin depicting the cytoskeleton are illustrated in FIGS. 6A and 6B. The cells show distinctly different phenotypes when cultured on the different substrates. The nuclei are elongated along the fibers and much more rounded on the flat, 2D surface (FIG. 6A). Protein F-actin is shown expanding in web-like morphology across the fibers (FIG. 6B) and aligning unidirectionally on the 2D surface. Immunofluorescence staining of gap junction protein connexin-43 illustrated in FIG. 7B, shows good cell-cell communication occurring across the fibers in the 3D fiber scaffold and elongation of the nuclei attached to each fiber compared to a 2D polystyrene surface as illustrated in FIG. 7A. The expression of focal adhesion protein, vinculin, shown in FIG. 7 (red), indicates the sites of attachment to the extracellular matrix.

Figure 9:
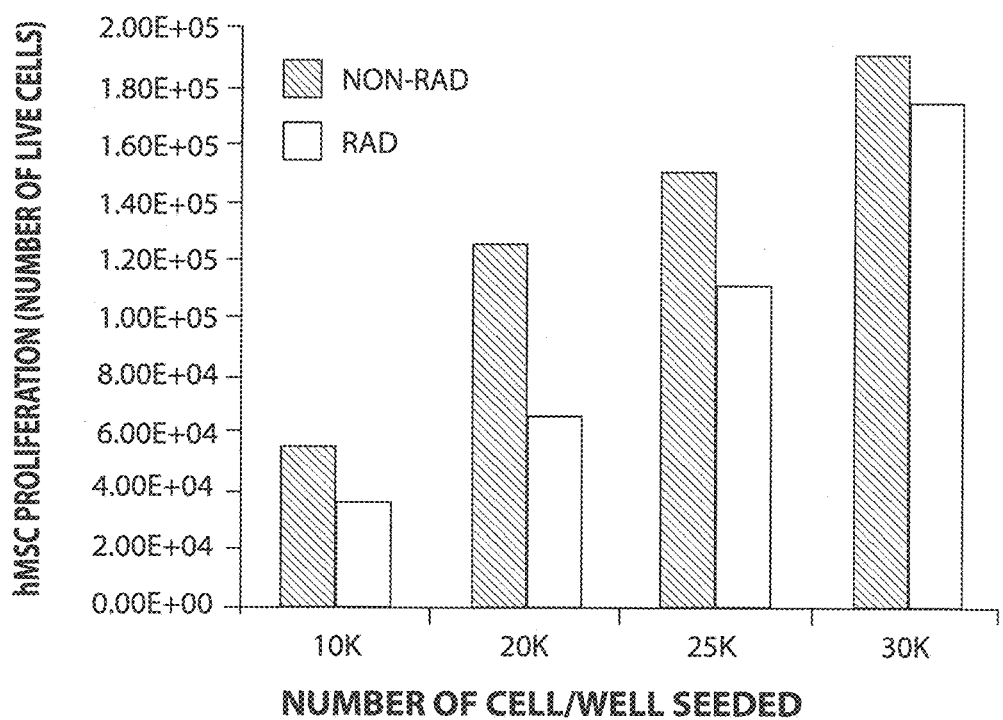
FIG. 9 is a graph showing the results of cells that were seeded (10K-30K cells/well) irradiated for 48 hours, and cell count determined by trypan blue excursion.
Figure 10:
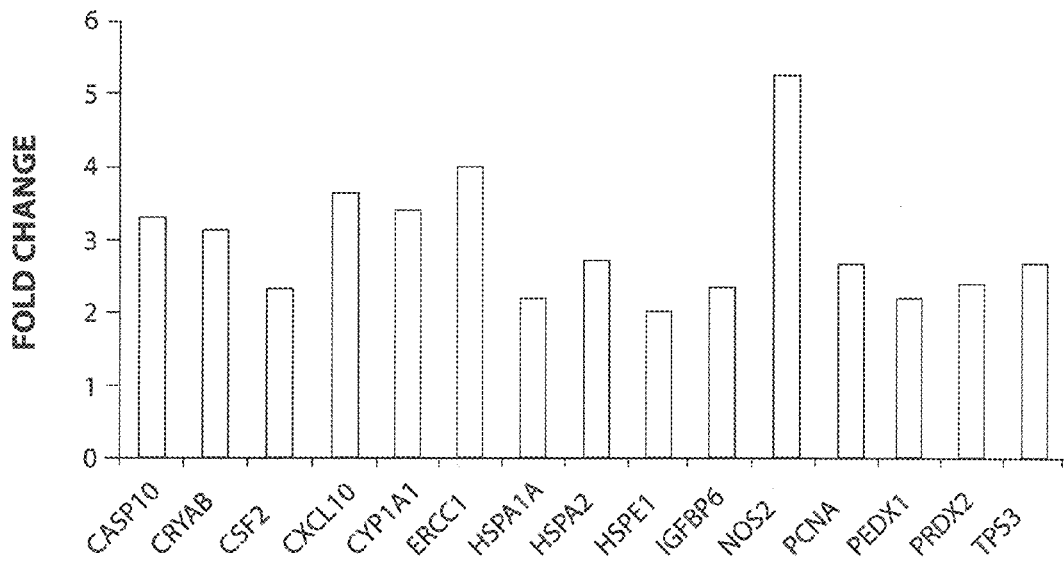
FIG. 10 is a chart showing genes downregulated after 48 hour exposure to radiation.
Figure 11:
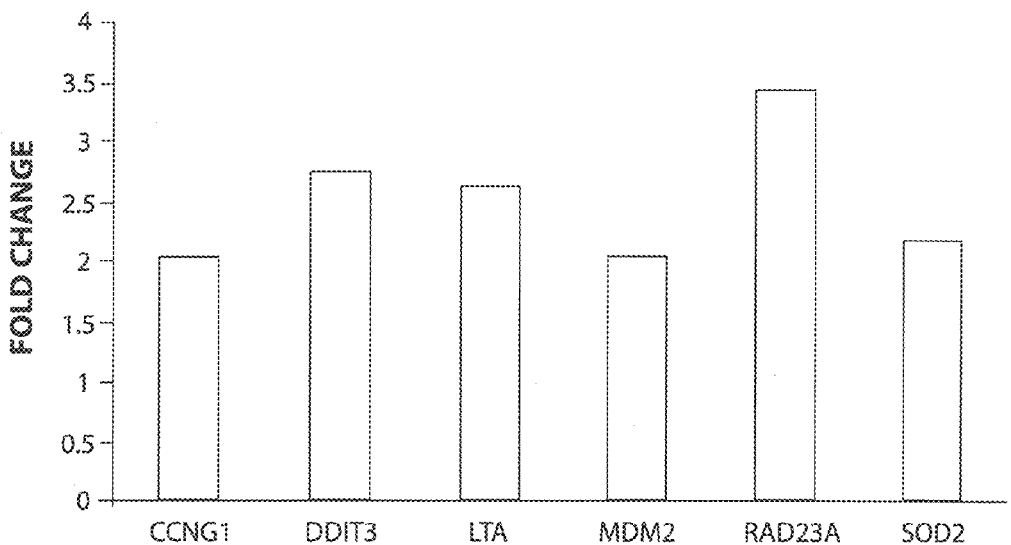
FIG. 11 is a chart showing genes upregulated after 48 hours exposure to radiation.

Due to the intrinsic electrical properties associated with the 3D fiber scaffold, protein expression specific to electrically active cells was examined. hMSCs were cultured on various 2D surfaces including CP2 (polyimide) film, PVDF film, coverslip (control) and coverslip conditioned with retinoic acid (positive control), 3D fiber surfaces fabricated from CP2 and PVDF. Microtubule associated protein (MAP2) was probed using Western blot. Gel images (not shown) indicate that the protein was upregulated for all surfaces after 7 days in culture with fibers continuing to upregulate MAP2 after 14 days in culture and the 2D surfaces downregulating the protein. The 3D fiber scaffolds expressed MAP2 2.5 fold more than the positive control conditioned with retinoic acid after 14 days in culture. These results demonstrate the significant influence the in vitro model has on gene and protein expression and how the various materials and architecture contribute to intracellular signaling, cell-cell communication and cytoskeleton organization.

hMSCs are considered radioresistant, potentially in part due to a resistance to apoptosis and DNA repair responses when exposed acutely to gamma radiation. In contrast, the effect of chronic, low dose radiation on hMSC has not been thoroughly studied. Preliminary data generated in tissue culture polystyrene (TCPS) suggest chronic exposure (48 hr) to $\gamma$-radiation (0.1541 Gy/hr) under static conditions decreased hMSC proliferation (FIG. 9). There was no increase in cell death observed by trypan blue exclusion (data not shown). Focused microarrays were used to analyze genes and pathways associated with cellular stress. A comparison between cells cultured on TCPS with and without radiation after 48 hours is shown in FIGS. 10 and 11. Downregulation of 15 genes was observed while six genes were upregulated including superoxide dismutase (SOD2) which has been reported by several researchers as a key gene expressed during radiation exposure. RAD23A, a protein involved in nucleotide excision repair, was upregulated more than 3 fold although ERCC1 which is also involved in nucleotide excision repair was downregulated. Overall, the genetic changes that occurred during this pilot study provided important information that needs further examination to understand what is occurring at the genetic level during chronic exposure. The downregulation of tumor suppressor protein p53 and upregulation of MDM2 suggest a degradation in the p53 protein associated with MDM2 binding. PRDX1 and PRDX2 are linked to antioxidants that play protective roles in cells. Both genes were downregulated having negative implications since a recent study reported that mice lacking PRDX1 produce more cellular reactive oxygen species (ROS) which plays a role in cancer development or progression. It will be important in future studies to probe deeper into ROS production and the role of p53 during chronic radiation exposure. This observation set the precedent for observable differences between non-irradiated and chronic, low dose $\gamma$-irradiated hMSC.

A first study according to the present invention was performed to verify the 3D scaffold 1 (FIG. 2) was compatible with the simulated microgravity bioreactor 10 (FIG. 1). Human mesenchymal stem cells were seeded at 200,000 cells/mL onto the 3D scaffold 1 and allowed to incubate for a minimum of thirty minutes prior to loading onto the bioreactor 10. A Synthecon RCCS-4CS bioreactor with 4 mL vessels was used to simulate microgravity. The pre-seeded scaffolds 1 were placed in the bioreactor 10 along with fresh media and rotated at 22 RPM in a 5% $CO_2$, 37° C. humidified incubator for 48 hours. After 48 hours, the samples were removed and RNA extracted using RNEASY minikit. Cell stress and toxicity focused microarrays were used to analyze the gene expression. The scaffold 1 in the microgravity bioreactor 10 was compared to the same scaffold under static conditions. Preliminary results indicated upregulation of heat shock proteins HSPA2 and HSPE1 which have been reported by several researchers in previous studies and has been hypothesized to protect against apoptosis. Two additional genes that showed significant change were Annexin A5 and insulin-like growth factor binding protein-6. Only one gene showed a significant downregulation when comparing the two environments, XRCC1, which is involved in DNA repair. This is not surprising since one would not expect to see considerable DNA damage in the absence of radiation. The first study verified that the cells can be cultured on the scaffold 1 successfully using the microgravity bioreactor 10 and that there are notable changes between the static and microgravity conditions.

A second study according to the present invention was performed to validate the experimental set-up 25 (FIG. 1). hMSCs were seeded on the 3D scaffold 1 and allowed to incubate for a minimum of 30 minutes. The pre-seeded scaffolds 1 were placed in the bioreactor 10 along with fresh media and rotated at 22 RPM in a 5% $CO_2$, 37° C. humidified incubator 12 for 48 hours. The incubator 12 was specially designed with a plexiglass door to accommodate radiation experiments. Dosimetry for the set-up involved analyzing alanine pellets in both the microgravity bioreactor 10 and static tissue culture dishes. The microgravity bioreactor 10 set-up was positioned at a distance from the Co-60 radiation source 14 to deliver a total of 7.4 Gy of chronic gamma radiation over a period of 48 hours. After 48 hours, the samples were removed and RNA extracted using RNEASY minikit to verify the set-up.

Radiation and microgravity are extreme stressors that humans will be chronically exposed to during future long duration space missions. Determining the impact of chronic low-dose radiation exposure coupled with simulated microgravity will assist in understanding the underlying mechanisms associated with each stressor as well as determine the extent to which combined effects may exist. Uncovering the mechanisms will help lead to more effective countermeasures to protect crew health while studying these effects in a more realistic 3D environment and provide a clearer indication of the changes expected in vivo.

The overall objectives of the present invention/study are to determine 1) if there are synergistic effects resulting from combined radiation and microgravity stressors, 2) an understanding of the influence of the in vitro cell culture environment by examining two different 3D scaffolds and comparing them to conventional 2D tissue culture environment and 3) obtain an understanding of the effect of return to earth and changes associated with that stressor. An experiment on the ISS that closely mimics the ground based set-up of the present invention will help to determine if the simulated microgravity bioreactor along with the biomimetic 3D scaffold provide a suitable analog for future ground-based microgravity studies. Another objective of the present invention is to establish baseline studies to not only to compare to ISS, but to other irradiation facilities that can do low level chronic exposure.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

All ranges disclosed herein are inclusive of the endpoints, and the endpoints are independently combinable with each other. Each range disclosed herein constitutes a disclosure of any point or sub-range lying within the disclosed range.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." As used herein, the term "and/or" includes any and all combinations of one or more of the associated listed items. As also used herein, the term "combinations thereof" includes combinations having at least one of the associated listed items, wherein the combination can further include additional, like non-listed items. Further, the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

Reference throughout the specification to "another embodiment", "an embodiment", "exemplary embodiments", and so forth, means that a particular element (e.g., feature, structure, and/or characteristic) described in connection with the embodiment is included in at least one embodiment described herein, and can or cannot be present in other embodiments. In addition, it is to be understood that the described elements can be combined in any suitable manner in the various embodiments and are not limited to the specific combination in which they are discussed.

What is claimed is:

1. An assembly for identifying combined effects of microgravity and radiation, the assembly comprising:
a bioreactor comprising a rotating wall vessel configured to simulate reduced gravity in a test space therein; and
a gamma radiation source configured to provide steady gamma radiation, wherein a specimen disposed in the test space is exposed to the gamma radiation, the specimen including at least one of: cells, bacteria and viruses.

2. The assembly of claim 1, including:
a three dimensional scaffold disposed in the test space, the three dimensional scaffold comprising a plurality of polymer fibers configured to mimic an in vivo environment.

3. The assembly of claim 2, wherein:
the three dimensional scaffold comprises polymer fibers.

4. The assembly of claim 3, wherein:
the polymer fibers are disposed in a plurality of layers having an alternating 0°/90° layup.

5. The assembly of claim 2, wherein:
the polymer fibers comprise electrospun polyvinylidene fluoride.

6. The assembly of claim 1, wherein:
the gamma radiation source provides the gamma radiation at a controlled rate.

7. The assembly of claim 6, wherein:
the gamma radiation source provides a low dose radiation at a rate of about 500 µGy/day.

8. The assembly of claim 1, including:
a cell culture disposed in the rotating wall vessel.

9. The assembly of claim 8, wherein:
the cell culture comprises human fibroblast cells.

10. The assembly of claim 8, wherein:
the cell culture comprises human mesenchymal stem cells.

11. The assembly of claim 1, including:
an incubator defining a temperature-controlled internal space; and wherein:
the rotating wall vessel of the bioreactor is disposed inside the internal space, and wherein the gamma radiation source is disposed outside the internal space adjacent the incubator whereby the steady gamma radiation from the gamma radiation source is directed into the internal space.

12. A method comprising:
providing a cell culture in a ground-based test environment;
exposing the cell culture to gamma radiation from a gamma radiation source while the cell culture is simultaneously exposed to simulated microgravity from a bioreactor comprising a rotating wall vessel configured to simulate reduced gravity in the ground-based test environment; and
determining a response of the cell culture to combined environmental stressors from exposure to the gamma radiation and exposure to the simulated microgravity.

13. The method of claim 12, wherein:
the cell culture comprises human mesenchymal stem cells.

14. The method of claim 13, further comprising:
determining effects of combined microgravity and radiation on the cell culture with respect to gene expression.

15. The method of claim 12, wherein:
the cell culture comprises a three dimensional macroporous fibrous structure.

16. The method of claim 15, wherein:
the three dimensional macroporous fibrous structure comprises polymer fibers.

17. The method of claim 16, wherein:
the polymer fibers comprise electrospun polyvinylidene fibers.

18. The method of claim 12, wherein:
the gamma radiation source provides low dose gamma radiation at a rate of about 500 µGy/day.

19. The method of claim 12, wherein:
a response of the cell culture is utilized to develop a treatment for diseases.

20. The method of claim 19, wherein:
the cell culture comprises at least one bacteria, and an expression of genes in response to the combined environmental stressors is utilized to develop a vaccine.

* * * * *